(12) United States Patent
Homman et al.

(10) Patent No.: US 8,218,834 B2
(45) Date of Patent: Jul. 10, 2012

(54) METHOD OF ANALYZING CELL STRUCTURES AND THEIR COMPONENTS

(75) Inventors: Mohammed Homman, Nacka (SE); Ida-Maria Sintorn, Laholm (SE)

(73) Assignee: Intelligent Virus Imaging Inc., Salem, OR (US)

( * ) Notice: Subject to any disclaimer, the term of this patent is extended or adjusted under 35 U.S.C. 154(b) by 1230 days.

(21) Appl. No.: 11/911,274

(22) PCT Filed: Feb. 17, 2006

(86) PCT No.: PCT/US2006/005571
§ 371 (c)(1),
(2), (4) Date: Oct. 11, 2007

(87) PCT Pub. No.: WO2006/112928
PCT Pub. Date: Oct. 26, 2006

(65) Prior Publication Data
US 2008/0205740 A1 Aug. 28, 2008

Related U.S. Application Data

(60) Provisional application No. 60/594,526, filed on Apr. 15, 2005.

(51) Int. Cl.
*G06K 9/00* (2006.01)
(52) U.S. Cl. ........................ 382/128; 382/170
(58) Field of Classification Search ........................ None
See application file for complete search history.

(56) References Cited

U.S. PATENT DOCUMENTS

| | | | |
|---|---|---|---|
| 6,063,580 A | | 5/2000 | Maiese et al. |
| 6,163,622 A | * | 12/2000 | Abdel-Mottaleb et al. ... 382/170 |
| 7,034,299 B2 | * | 4/2006 | Nakagaki et al. ............. 250/311 |
| 7,039,255 B2 | * | 5/2006 | Lee et al. ...................... 382/305 |
| 7,627,178 B2 | * | 12/2009 | Suzuki et al. ................. 382/190 |
| 2002/0081026 A1 | * | 6/2002 | Izume et al. .................. 382/170 |
| 2004/0240733 A1 | * | 12/2004 | Hobson et al. ................ 382/170 |
| 2005/0013471 A1 | * | 1/2005 | Snoeren et al. ............... 382/131 |
| 2006/0088212 A1 | * | 4/2006 | Ohmi et al. ................... 382/170 |

(Continued)

OTHER PUBLICATIONS

Clayton et al., "Analysis of Antigenicity and Topology of E2 Glycoprotein Present on Recombinant Hepatitis C Virus-Like Particles", J Virol. Aug. 2002; 76(15): 7672-7682, doi: 10.1128/JVI.76.15.7672-7682.2002. Available online: http://www.ncbi.nlm.nih.gov/pmc/articles/PMC136371/.*

(Continued)

*Primary Examiner* — Bhavesh Mehta
*Assistant Examiner* — Tahmina Ansari
(74) *Attorney, Agent, or Firm* — Fasth Law Offices; Rolf Fasth

(57) ABSTRACT

A cell is provided that contains a plurality of virus particles. A first image of a first virus particle and a second image of a second virus particle are taken by electron microscopy technology. The first virus particle is characterized as being in a first maturity stage and the second virus particle as being in a second maturity stage. The first image and the second image are transformed to first and second gray scale profiles, respectively, based on pixel data. The first and second gray scale profiles are then saved as first and second templates, respectively. A third virus particle in a third image is identified. The third image is transformed into a third gray scale profile. The third gray scale is compared to the first and second template to determine a maturity stage of the third virus particle.

10 Claims, 1 Drawing Sheet

U.S. PATENT DOCUMENTS

| | | | | |
|---|---|---|---|---|
| 2006/0262977 A1* | 11/2006 | Mitsui | | 382/209 |
| 2007/0031034 A1* | 2/2007 | Rising et al. | | 382/170 |
| 2008/0205740 A1* | 8/2008 | Homman et al. | | 382/133 |
| 2008/0212880 A1* | 9/2008 | Homman et al. | | 382/209 |
| 2009/0208082 A1* | 8/2009 | Westerhoff et al. | | 382/131 |
| 2009/0324075 A1* | 12/2009 | Shiiyama | | 382/170 |
| 2010/0111416 A1* | 5/2010 | Meiers | | 382/170 |
| 2010/0151446 A1* | 6/2010 | Homman | | 435/5 |

OTHER PUBLICATIONS

Lata et al., "Maturation Dynamics of a Viral Capsid: Visualization of Transitional Intermediate States." Cell. Jan. 21, 2000, vol. 100, pp. 253-263.

Lua et al., "Virus Morphogenesis of *Helicoverpa armigera* Nucleoployhedrovirus in *Helicoverpa zea* Serum-Free Suspension Culture." Journal of General Virology. 2000, vol. 81, pp. 2531-2543.

* cited by examiner

METHOD OF ANALYZING CELL STRUCTURES AND THEIR COMPONENTS

PRIOR APPLICATION

This application is a U.S. national phase application based on International Application No. PCT/US2006/005571, filed 17 Feb. 2006, claiming priority from U.S. Provisional Patent Application No. 60/594,526, filed 15 Apr. 2005.

TECHNICAL FIELD

The present invention relates to a method of analyzing cell structure that includes virus morphologies.

BACKGROUND OF INVENTION

Many efforts have been made in the past to classify and analyze cell structures that include viruses and other components. Various image analysis methods have been developed to describe, segment and classify viruses by using available image technologies. For example, cryo-electron microscopy has been used but the structures of the cells and the virus particles are not shown very well. It has also been difficult to objectively, repeatedly and reliably describe the cell components to accurately determine the maturity stages of the cell components. This partly explains why the previous analysis methods have not been very effective and there is a need for more effective methods for analyzing cell and virus particle structures.

SUMMARY OF INVENTION

The method of the present invention provides a solution to the above-outlined problems. More particularly, the method of the present invention is for analyzing cell structures and their components. A cell structure may be provided that contains a plurality of virus particles. A first image of a first virus particle and a second image of a second virus particle may be taken by using an electron microscopy technology. The first virus particle is characterized as being in a first maturity stage and the second virus particle as being in a second maturity stage. The first and second images are transformed to first and second gray scale profiles, respectively, based on pixel data or other information from the images. The first and second gray scale profiles are saved as first and second templates, respectively. A third virus particle in a third image may then be identified. The third image is transformed into a third gray scale profile. The third gray scale is compared to the first and second template to determine a maturity stage of the third virus particle.

DETAILED DESCRIPTION

With reference to FIGS. 1-4, the method of the present invention relates to steps for analyzing cell structures that include components such as virus particles. The analysis of virus particles is only used as an illustrative example of the method of the present invention and the invention is not limited to virus particles. Any suitable component in a structure such as a cell may be analyzed using the method. An important feature of the present invention is that different virus particles produce unique graphs or gray level profiles.

Also, the various virus particles may be in different maturity stages so that the present method may not only be used to determine the types of virus particles but also the maturity stage of the particular virus particle.

In general, an image 12 may first be taken by a suitable technique, such as transmission electron microscopy (TEM), of a cell structure 14. The image may include viral virus particles 16 that are at various maturity stages. For example, the virus particles may be categorized as being in three or more maturity stages including empty or quite immature virus particles, as shown in FIG. 2A, intermediary virus particles, as shown in FIG. 3A, and more mature virus particles, as shown in FIG. 4A.

The virus particles 16 are often linearly deformed making the virus particles look slightly like ellipses rather than circles. To be able to make an accurate radial density profile it is desirable that the virus particles are radially symmetrical. Thus, the deformation has to be inverted in order to achieve the best results when the analysis of the present invention is performed. This may be done by fitting an ellipse to the viral virus particle which is assumed to be approximately circular. The principal radii and the orientation of the ellipse may be used to determine the deformation and to make the inverse deformation.

Every pixel position in the old elliptic image is then transformed into the new image to produce a picture where the virus particle structures are circular. All virus particle structures are preferably subject to this deformation adjustment. As described below, the radially symmetric virus particle structure may be transformed to a gray-level profile.

It may be used to describe the structure by calculating the mean gray-level at each distance from the center going from the center and out towards a periphery or shell of the virus particle structure. The transformation to circular structures is particularly useful when measuring the particle radius and the thickness of the virus particle walls.

Figure 1:
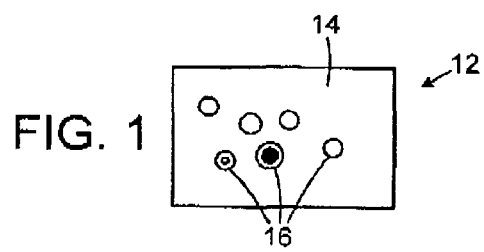
FIG. 1 is a schematic view of a cell nucleus containing virus particles.
Figure 2B:
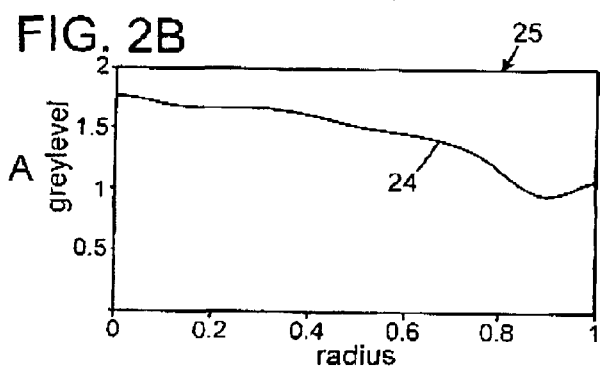
FIG. 2B is a schematic view of a gray scale profile of the virus particle shown in FIG. 2A.
Figure 2A:
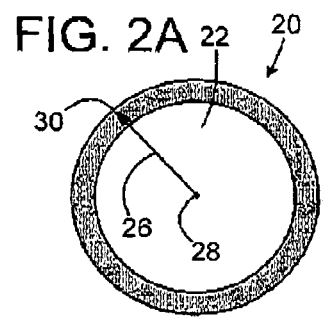
FIG. 2A is a microscope image of a virus virus particle in a first maturity stage.

More particularly, FIG. 2A shows an image 20 of a relatively immature or empty viral virus particle 22 in a cell nucleus and FIG. 2B shows its corresponding gray level profile 24 in a graph 25. It is also possible to develop mathematical algorithm to describe the virus particle structures instead of relying on gray scale profiles. Viral DNA may be inserted into the virus particle 22 that may eventually develop into a mature virus particle with a dense DNA core, as shown in FIG. 4A and discussed below.

The virus particle 22 has a radius 26 that extends from the center 28 radially outwardly to a center of the shell wall 30 of the virus particle. Since the virus particle 22 is virtually empty of virus components, the center portion is almost white which shows as a high gray level value of the profile 24 on the left side of the graph 25. The shell 30 is darker so the profile 24 has a gradually lower gray level value on the right side of the graph 25 since the shell area corresponds to the right side of the graph 25.

Figure 3B:
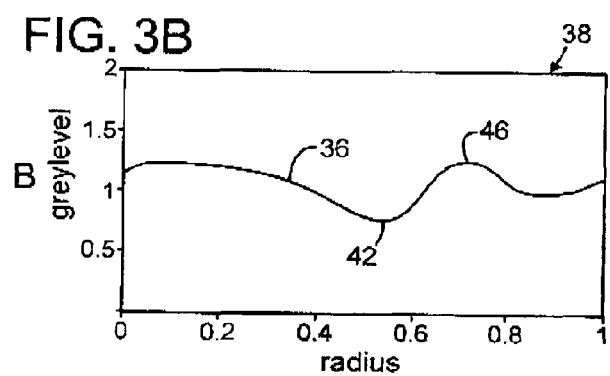
FIG. 3B is a schematic view of a gray scale profile of the virus particle shown in FIG. 3A.
Figure 3A:
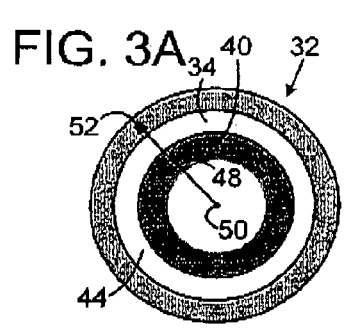
FIG. 3A is a microscope image of a virus virus particle in a second maturity stage.

FIG. 3A shows an image 32 of a virus particle 34 that is not fully mature. The virus particle 34 contains an additional viral protein that helps in the packaging of viral DNA into the virus particles. The virus particle walls may include protein layers so that the size of the virus particle and the thickness of the layers may be determined. FIG. 3B shows a corresponding gray level profile 36 in a graph 38. The virus particle 34 has a radius 48 that extends from a center 50 to a center of a peripheral shell 52 of the virus particle. The black or dark ring 40 is shown as a local minimum 42 in the profile 36 while the white ring 44 is shown as a local maximum 46 in the profile 36. The beginning and the end of the rings and shell wall may be determined by analyzing the second derivative of the gray scale profiles.

Figure 4B:
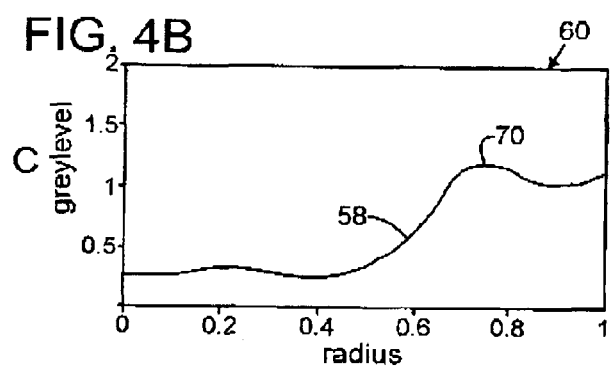
FIG. 4B is a schematic view of a gray scale profile of the virus particle shown in FIG. 4A.
Figure 4A:
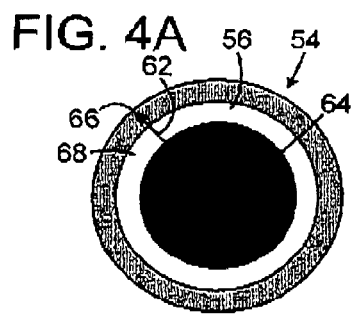
FIG. 4A is a microscope image of a virus virus particle in a third maturity stage.

Similarly, FIG. 4A shows an image 54 of a more mature virus particle 56 and FIG. 4B shows the corresponding gray level profile 58 in a graph 60. The virus particle 56 has a radius 62 that extends from a center 64 to a center of a peripheral shell wall 66 of the virus particle 56. The white ring 68 is shown as a local maximum 70 in the profile 58.

An important feature of the method of the present invention is that it is possible to create templates based on the gray scale profiles to objectively describe the virus virus particles. The templates may be created by using mathematical methods also. For example, a template may be based on an average of the characteristics of many virus particles that are in the same maturity stage. The templates may then be saved in a database and later be retrieved when it is time to analyze and characterize new images containing virus particles. When thousands of images are taken, the templates may be used to calculate the number of virus particles at the various maturity stages. In this way, the virus production in a cell may be quantified by taking additional TEM images.

More particularly, template gray level profiles of intermediate virus particles may be created and used to identify these particles in electron micrographs. To create the template gray profile, the center point together with the approximate size of the virus particle must be known. The approximate size (radius) in pixels of the virus particle can be deduced from knowing the magnification of the image and the actual true size of the virus particle, or it can be marked in the image. The center point of an object can be marked manually or found through template matching. Preferably, the center point is automatically chosen as the center of the ellipse after deformation adjustment. As described above, the gray-level profile can be visualized as a curve profile where peaks in the curve represent bright radial regions and valleys represent dark radial regions.

The width of certain radial features, such as the virus particle shell, can give information regarding the extent of tegumentation of the virus particle when measurements are applied to cytoplasmic virus particle forms. The problem with measuring this thickness directly from the image or the profile is the difficulty of determining where the virus particle begins and ends. Gradient information about the profile can be used to solve this problem. The first gradient measures how the gray-levels change along the curve. If the gray-levels move from dark to bright along the profile the gradient will have positive values and if the gray-levels move from bright to dark the gradient will have negative values. Where there is no change at all or where the profile has a local maximum or minimum, the gradient will be 0. The thickness of the shell could, hence, be described as the number of pixels between the local minimum to the local maximum in the gradient. This is an objective way of measuring where the shell begins and ends. To find these extreme points, the second gradient (the gradient of the gradient curve) is calculated since a local maximum or minimum will be zero in the gradient curve.

In this way, gray level profiles are generated for the many virus particles. The generated gray level profile curves may be smoothed by convolution with a standard Gauss function.

The curves behavior at the virus particle wall or virus particle shell may be depicted as a valley relative to the linear behavior representing the overall virus particle structure.

The derivative of the function reaches a local minimum where the downward curve is the steepest which represent the start of the virus particle wall. There is a local maximum where the upward curve is the steepest which represents the end or outside of the virus particle wall. The locations of these local extremes are found as the zero-crossings of the second derivative of the profile and the distance between the extremes serve as the measurement of the width of the virus particle wall.

As discussed above, the radius of a virus particle is calculated as the distance between the center of the virus particle and the center of the virus particle wall. The center of the virus particle wall may be predicted as the minimum value in the Gauss smoothed profile which is the zero crossing of the $1^{st}$ gradient of the smoothed curve.

Another important feature is that the images may be taken again at a later time and new statistics of the maturity stages of the virus particles may be compared to the earlier statistics of the number of virus particles in the various maturity stages. This is of particular interest when the virus particles have been subjected to an active chemical substance such as a suitable pharmaceutical substance to better understand how the substance affects the virus production in the virus particles. For example, an existing or new substance may be used to determine which part of the virus production or which maturity stage is affected by or stopped by the substance. If, for example, the virus goes through six maturity stages and there is no virus in the fourth maturity stage it may be concluded that the pharmaceutical substance prevents the virus from maturing beyond the fourth maturity stage. The method may also be used to determine which maturity stage a new pharmaceutical should be designed to affect.

It is also possible to identify new different virus morphologies and describe how the new virus differs from earlier identified virus morphologies.

Another feature of the method of the present invention is that it is possible to remove certain proteins from the virus by using bio technical methods, such as siRNA, and then objectively determine how the removal of the protein or proteins affect the virus morphology and its corresponding gray scale profile. For example, a pharmaceutical substance may be designed to prevent the formation of a certain protein in the virus particle and the effects of such prevention on the gray scale profile can be studied. The removal of a certain protein may prevent the virus from advancing from one maturity stage to a later maturity stage. The method makes it possible to determine which maturity stage is affected by the removal of the particular protein.

While the present invention has been described in accordance with preferred compositions and embodiments, it is to be understood that certain substitutions and alterations may be made thereto without departing from the spirit and scope of the following claims.

The invention claimed is:

1. A method of analyzing maturity stages of a virus, comprising:

providing a cell containing a plurality of viral particles of a type of virus type;

taking a first image of a first viral particle and a second image of a second viral particle of the type of virus;

characterizing the first viral particle as being in a first maturity stage and the second viral particle as being in a second maturity stage;

transforming the first image to a first linear gray scale profile representing a radial density profile of the first viral particle going from a center of the first viral particle radially outwardly towards a periphery of the viral particle;

transforming the second image to a second linear gray scale profile;

saving the first gray scale profile as a first template;

saving the second gray scale profile as a second template;

identifying a third particle in a third image;

transforming the third image into a third gray scale profile; and comparing the third gray scale profile to the first and second template to determine a maturity stage of the third particle.

2. The method according to claim 1 wherein the method further comprises subjecting the third particle to an active chemical substance.

3. The method according to claim 1 wherein the method further comprises creating a fourth image of the third particle at a time later than a time of the creation of the third image.

4. The method according to claim 3 wherein the method further comprises determining a maturity stage of the third particle.

5. The method according to claim 4 wherein the method further comprises determining an effect of the chemical substance on the third particle based on the determined maturity stage.

6. The method according to claim 5 wherein the method further comprises transforming the fourth image to a fourth gray scale profile to objectively determine the effect of the chemical substance on the third particle.

7. A method of analyzing virus particles, comprising:

providing a plurality of virus particles;

taking a first image of a first virus particle and a second image of a second virus particle;

characterizing the first virus particle as being in a first maturity stage and the second virus particle as being in a second maturity stage;

transforming the first image to a first linear gray scale profile representing a radial density profile of the first viral particle going from a center of the first viral particle radially outwardly towards a periphery of the viral particle;

transforming the second image to a second gray scale profile;

identifying a third virus particle in a third image;

transforming the third image into a third linear gray scale profile; and comparing the third linear gray scale profile to the first and second linear gray scale profiles to determine a maturity stage of the third virus particle.

8. The method according to claim 7 wherein the method further comprises determining a beginning and an end of a virus particle wall by taking derivatives of the linear gray scale profile.

9. The method according to claim 7 wherein the method further comprises determining a beginning and an end of a protein layer by taking derivatives of the linear gray scale profile.

10. The method according to claim 7 wherein the method further comprises removing a protein from the virus particle and generating a modified gray scale profile.

* * * * *